United States Patent [19]

Abrams

[11] Patent Number: 4,792,621

[45] Date of Patent: Dec. 20, 1988

[54] METHOD FOR CONTINUOUS PRODUCTION OF AROMATIC CARBOXYLIC ACID

[75] Inventor: Kenneth J. Abrams, Naperville, Ill.

[73] Assignee: Amoco Corporation, Chicago, Ill.

[21] Appl. No.: 890,128

[22] Filed: Jul. 28, 1986

[51] Int. Cl.$^4$ .......................................... C07C 51/265
[52] U.S. Cl. .................................................. 562/414
[58] Field of Search ............................... 562/414, 416

[56] References Cited

U.S. PATENT DOCUMENTS 3,119,860  1/1964  Kalfadelis et al. ............... 562/416 X
4,593,122  6/1986  Hashizume et al. ................ 562/414

Primary Examiner—Michael L. Shippen
Attorney, Agent, or Firm—James R. Henes; William H. Magidson; Ralph C. Medhurst

[57] ABSTRACT

An improved method for continuously producing an aromatic carboxylic acid from an aromatic alkyl is disclosed. The reaction medium, contained within a pressurized reactor, includes an aqueous monocarboxylic acid solvent, the aromatic alkyl, and an oxygen-containing gas. Heat is generated in the reactor during the course of the oxidation reaction, and is removed from the reactor by vaporization of a portion of the reaction medium. The vaporized reaction medium that exits the pressurized reactor as a vapor is partitioned in a condenser system, which defines a reflux loop, into an aqueous partial condensate having a relatively lesser water-to-solvent weight ratio and a vapor phase having a relatively greater water-to-solvent weight ratio. At least a portion of the partial condensate is returned directly to the reactor as an aqueous direct reflux stream, while the vapor phase is withdrawn from the reflux as a vapor stream. The withdrawn vapor stream is then subjected to further heat exchange, as its vapor pressure is reduced to less than the oxidation reactor pressure, thereby producing an aqueous aliphatic acid stream having a greater water concentration and a greater water-to-solvent weight ratio than the direct reflux stream. Next, a predetermined portion of the aqueous aliphatic acid stream is combined, as an indirect recycle stream, with an aromatic alkyl feed mixture stream upstream of the oxidation reactor.

4 Claims, 1 Drawing Sheet

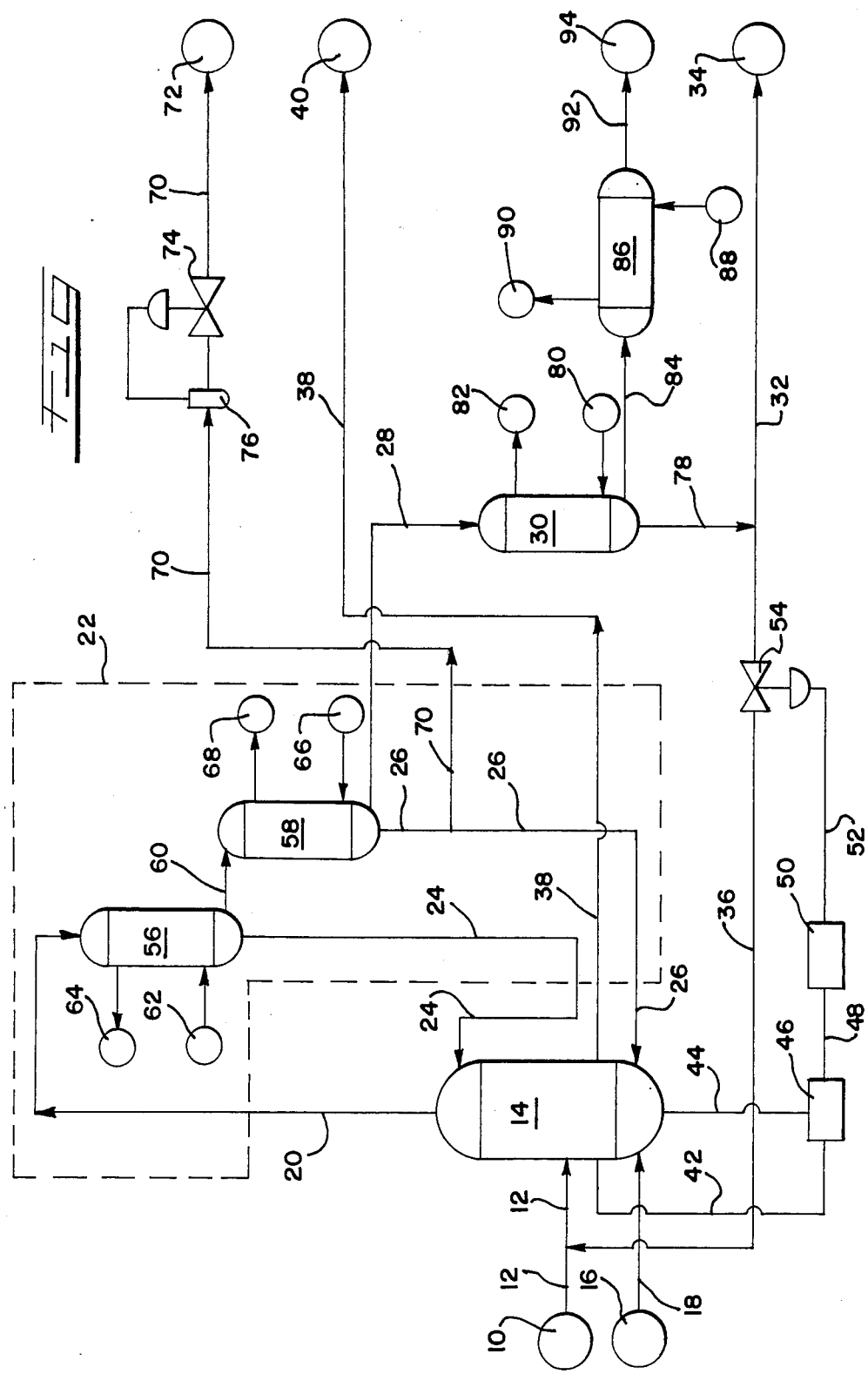

METHOD FOR CONTINUOUS PRODUCTION OF AROMATIC CARBOXYLIC ACID

TECHNICAL FIELD OF THE INVENTION

This invention relates generally to the continuous, liquid-phase oxidation of an aromatic alkyl to an aromatic carboxylic acid within an oxidation reactor and in the presence of an aqueous aliphatic acid solvent. In particular the present invention is directed to a method which readily permits modulation of water concentration in the reactor.

BACKGROUND OF THE INVENTION

Liquid-phase oxidation of an aromatic alkyl to an aromatic carboxylic acid is a highly exothermic chemical reaction. Typically, volatilizable aqueous solvents are employed to contain the reaction mixture and to dissipate heat of reaction.

Liquid-phase oxidation of aromatic alkyls to aromatic carboxylic acid conventionally takes place in a vented, well-mixed oxidation reactor equipped with an overhead condenser system. Such systems are shown in U.S. Pat. Nos. 3,170,768 and 3,092,658, both to Baldwin. A substantial portion of the reaction-generated heat is removed by evaporating a portion of the reaction mixture from the reactor, partially condensing it, and returning at least a portion of the condensate to the reactor.

In particular, an evaporated portion of the reaction mixture is withdrawn from the reactor head space. These vapors are then passed into an overhead condenser system that condenses a portion of these vapors and returns a resultant condensate stream to the reactor as reflux.

The non-condensed vapors that are discharged from the condenser system are then conventionally introduced into a shell-and-tube condenser of the knockback variety. In addition to condensing at least a portion of these condenser-system discharge vapors, the knockback condenser serves as a liquid-liquid separator to separate such condensed vapors into respective water-rich and solvent-rich phases. The solvent-rich phase is returned to the reactor as reflux. This solvent-rich reflux together with the earlier-mentioned condensate stream that is refluxed to the reactor from the overhead condenser system define a reflux loop.

Use of knockback condensers is undesirable for a variety of reasons. First, the liquid-liquid separator portion of the knockback condenser is provided with an internal baffle which separates a solvent-rich stream from a water-rich stream. Unscheduled process upsets or disturbances, which typically are costly, can arise when either one of the solvent-rich and water-rich streams carries over the baffle and combines with the other stream. Second, a knockback-type condenser can only accommodate a relatively limited gas velocity. That is, a gas velocity that is greater that a predetermined value typically gives rise to liquid entrainment into the knockback condenser overhead stream. Such entrainment has historically given rise to numerous process operating problems. Third, the thermal efficiency of a knockback condenser is not particularly desirable. For example, because of the relatively low gas throughput rate, heat transfer coefficients of a knockback type condenser are typically relatively low. Accordingly, there exists a need for other process system designs providing significantly higher heat transfer coefficients, which systems are able to provide relatively more efficient process control.

The present invention provides a method for continuously producing an aromatic carboxylic acid product that does not suffer from the foregoing problems. In the method of the present invention, the above-mentioned liquid-liquid separation step is not employed. Instead, the conventional knockback type of condenser is eliminated, a condenser having a significantly higher heat transfer coefficient can be utilized, and efficient control over the amount of water present in the reactor can be maintained. In particular, the present method enables utilizing a relatively more efficient condenser, such as a downflow-type condenser, in place of the knockback condenser. Because a condenser that does not function as a liquid-liquid separator can be used, upsets caused by liquid carryover are eliminated. The more efficient condenser, moreover, can be subjected to a relatively higher pressure drop than was allowable for the knockback type of condenser. This, in turn, permits relatively higher gas velocities through the condenser than had been possible employing the conventional knockback condenser.

In practicing the method of the present invention, the condenser produces a condensate that is relatively rich in water. A portion of the thus-produced water-rich condensate can be returned to the reactor feed, upstream of the oxidation reactor, to control water concentration within the oxidation reactor.

SUMMARY OF THE INVENTION

The present invention facilitates the control of water concentration in the oxidation reactor, reduces heat duty of the reactor overhead condenser system and thus permits the use of less costly process equipment, and also provides the potential for operating the oxidation reactor at relatively lower water concentrations. The method of this invention contemplates partitioning the vapors exiting the oxidation reactor into a partial condensate having a relatively lesser water-to-solvent weight ratio and a vapor phase having a relatively greater water-to-solvent weight ratio. At least a portion of the partial condensate is returned directly to the reactor as a direct reflux stream while the vapor phase is withdrawn from the existing reflux loop as a vapor stream. The withdrawn vapor stream is then subjected to further heat exchange, while the vapor stream pressure is decreased to less than the oxidation reactor pressure, to produce an aqueous aliphatic acid stream having a water-to-solvent weight ratio greater than that of the direct reflux stream. Next, a predetermined portion of the aqueous aliphatic acid stream is combined, as an indirect recycle stream, with an aromatic alkyl feed stream upstream of the oxidation reactor.

Additional advantages or features of the present invention will be discussed below.

BRIEF DESCRIPTION OF THE FIGURE

The accompanying FIGURE is a process flow diagram illustrating a system embodying the principles of the method of the present invention.

DETAILED DESCRIPTION OF PREFERRED EMBODIMENT

While the present invention is susceptible to embodiment in various forms, there is shown in the accompanying FIGURE and hereinafter described in detail a preferred embodiment of the invention. The present disclosure is to be considered as an exemplification of the invention without limitation to the specific embodiment illustrated, however.

Referring to the accompanying FIGURE, reactor feed mixture from source 10 is introduced via conduit 12 into oxidation reactor 14. The reactor feed mixture comprises an aromatic alkyl, an aqueous monocarboxylic $C_2$ to $C_6$ aliphatic acid solvent, and a suitable oxidation catalyst. The feed mixture may further include a suitable promoter. An oxygen-containing gas under pressure from source 16 is separately introduced into reactor 14 via a conduit 18. The preferred oxygen-containing gas is air. The reactants in reactor 14 are maintained at an elevated pressure sufficient to maintain the contained, volatilizable reaction medium substantially in the liquid state at the reaction temperature.

Reactor 14 is a pressurized oxidation reactor vessel wherein liquid-phase oxothermic oxidation of the aromatic alkyl by the oxygen-containing gas takes place in the presence of the oxidation catalyst. The reaction medium contained by reactor 14 thus comprises the oxygen-containing gas, the aromatic alkyl that is to be oxidized to an aromatic carboxylic acid product, the catalyst, and a relatively volatile solvent.

During the course of the oxidation reaction, exothermic heat of reaction, generated by oxidation of the aromatic alkyl, is removed from reactor 14 by vaporization of a portion of the reaction medium. These vapors pass upwardly through reactor 14 and are introduced via a conduit 20 into a condenser system 22 that condenses a major portion of these vapors. The resultant condensate is returned to reactor 14 by pipelines 44 and 26.

The condenser system 22 defines a reflux loop for reactor 14 and includes a pair of condensers 56 and 58. Condensers 56 and 58 are each of the downflow type, and are connected in series by a pipeline 60. Preferably, each of the condensers 56 and 58, and the heat exchanger 30 are of the shell-and-tube variety.

The reactor vapors which are not condensed within the reflux loop are withdrawn from this loop and subjected to further heat exchange. Such vapors are introduced via conduit 28 into heat exchanger 30 which, in turn, cools the non-condensed reactor vapors and at the same time decreases the vapor pressure of these vapors, thereby producing an aqueous aliphatic acid liquid stream that has a water-to-solvent weight ratio and water concentration greater than that of the direct reflux stream.

A portion, or all, of the aqueous aliphatic acid liquid stream is recycled to conduit 12 via conduit 36 and thereafter combined with the reactor feed mixture upstream of reactor 14. In this manner, the water concentration of the reaction medium contained within reactor 14 can be readily and expeditiously controlled.

In operation, reactor 14 continuously produces an aromatic carboxylic acid product that is continuously withdrawn from reactor 14 and conveyed via a pipeline 38 to a suitable storage or processing facility 40. Concurrently, the amount of water in reactor 14 is regulated by valve 54 by splitting the condensate from heat exchanger 30 into a stream returned to reactor 14 via conduit 36 and another stream passed on to solvent recovery means 34 via conduit 32.

Suitable aromatic alkyls useful as reactor feed-mixture components or ingredients in the method of the present invention include toluene, o-xylene, m-xylene, p-xylene, and the triethybenzenes. The respective aromatic carboxylic acid products of these aromatic alkyls are benzoic acid, orthophthalic acid, isophthalic acid, terephthalic acid (TPA), and the benzenetricarboxylic acids. The method of this invention can be used to produce TPA, isophthalic acid, and trimellitic acid (1,2,4-benzenetricarboxylic acid). It is particularly well suited for the production of TPA.

Suitable aqueous aliphatic acid solvents useful in the method of this invention are those that are readily volatilizable at the reaction temperatures. Among such solvents are aqueous solutions of $C_2$ to $C_6$ monocarboxylic acids, e.g., acetic acid, propionic acid, n-butyric acid, isobutyric acid, n-valeric acid, trimethylacetic acid, caproic acid, and mixtures thereof. Preferably, the volatilizable monocarboxylic aliphatic acid solvent is an aqueous acetic acid solution.

Suitable catalyst systems, for present invention purposes, can include any catalyst system conventionally used for liquid-phase oxidation of an aromatic alkyl. A suitable catalyst system, e.g., may include a mixture of cobalt, manganese and bromine compounds or complexes, soluble in the particular volatilizable aqueous solvent employed. A preferred catalyst system is a solution prepared from dry cobalt, selected manganese acetates, and water. A preferred catalyst system may also include a promoter such as aqueous hydrogen bromide.

As an example, as p-xylene is oxidized to produce TPA practicing the method of the present invention, the usual process conditions and parameters can be summarized as follows: The contents of reactor 14 are subjected to a pressure in the range of about 15 to about 20 kg./cm.$^2$a. (about 215 to about 285 psia) at a temperature in the range of about 190° to about 210° C. (about 375° to about 410° F.). In the conventional process, however, the oxidation reactor contents usually are subjected to a pressure of about 27.1 kg./cm.$^2$ a. (about 385 psia) at a temperature of about 224° C. (about 435° F.).

Reduction of oxidation reactor pressure provides both capital-cost and operating-cost savings over the conventional process. Stainless steel can be used as a material of construction for a heat exchanger instead of titanium. Capital and operating savings can be realized by employing as the oxidation reactor a pressure vessel having a relatively lower pressure rating, thinner walls, less weight, etc. The capital and operating costs of the air-compressor can also be reduced as a result of relatively lower process pressures.

Moreover, operation at a lower reactor temperature provides a benefit in the form of improved reactor-seal life A reactor-seal failure typically gives rise to undesirable process downtime and aliphatic acid solvent loss, both of which are economically undesirable.

Another advantage or feature of the present invention is that the water concentration of the reaction medium contained by reactor 14 can be more easily controlled than conventionally possible. For example, if the amount of aqueous aliphatic acid returned to reactor 14 via pipeline 36 is minimized, water concentration of the reaction medium within reactor 14 can be maintained as low as about 7.5 weight percent. Typically, however, water concentration within reactor 14 is controllably maintained at a greater value, for example, in the range of about 12 to about 16 weight percent water, preferably in the range of about 12 to about 14 weight percent water.

To control water concentration of the reaction medium, a suitable aliquot sample can be extracted from reactor 14. The sample can be obtained employing, e.g., a side-mounted conduit 42 or a bottom-mounted conduit 44, either of which can be connected to a suitable conventional analyzer 46 adapted to perform the analysis and transmit the results thereof via communication link 48 to a suitable process-control unit such as a microprocessor unit 50. One such commercially available process-control unit is adapted to produce a pneumatic signal that can be conveyed via conduit 52 to an automatic flow-control valve 54 that, in turn, controls the flow of a liquid aqueous aliphatic acid stream. When automatic valve 54, or the like, is incorporated in pipeline 36 as shown in the accompanying FIGURE, the sampling of the reaction medium can determine the amount of water to be returned to reactor 14 as a portion of the aqueous aliphatic acid stream discharged from heat exchanger 30. Control of the water concentration in reactor 14 within desired limits is thus achieved. The predetermined portion of the aliphatic acid stream is returned to reactor 14 as an indirect recycle stream, upstream of reactor 14 as discussed hereinabove.

In operation, the vaporized reaction medium exiting reactor 14 via conduit 20 is primarily constituted by vaporized acetic acid ad water. Small amounts of the starting material, catalyst and reaction by-products are also present. About 80 weight percent of the vaporized reaction medium supplied by conduit 20 is condensed in downflow condenser 56 and returned via pipeline 24 to an upper portion of reactor 14 as a reflux. Such reflux typically is in the range of about 18 to 20 weight percent water and has a water-to-solvent weight ratio of about 0.2. That portion of the vaporized reaction medium vapors supplied by conduit 20 and not condensed in condenser 56 is introduced into downflow condenser 58 via pipeline 60. The non-condensed vapor stream within pipeline 60 typically has a water-to-solvent weight ratio of about 0.4. About 10 to about 12 weight percent of the vaporized reaction medium, supplied by conduit 20, is condensed in condenser 58 and returned via pipeline 26 to a lower portion of reactor 14 as liquid reflux. This condensed reflux stream contains about 25 weight percent water and has a water-to-solvent weight ratio of about 0.3. A portion of the total condensate in pipeline 26 can be withdrawn therefrom via a conduit 70 as a trim stream and supplied to a suitable storage or further processing facility 72. The remainder is returned to reactor 14 to control the water concentration of the reaction medium. Liquid flow through conduit 70 is controlled in a conventional manner employing an automatic flow-control valve 74 operatively connected to a liquid flow rate-indicating device 76.

A typical temperature of the vapor being introduced into condenser 56 via conduit 20 is about 199° C. (about 390° F.). Condenser 56 reduces the temperature of that vapor to about 166° C. (about 331° F.). Such cooled vapor, introduced into condenser 58 via pipeline 60, is then cooled further by condenser 58 to about 141° C. (about 286° F.)

A suitable heat-transfer medium from a source 62 is passed through downflow condenser 56 for the purpose of condensing process vapors contained therein, add is returned to a suitable reservoir 64. Similarly, a suitable heat-transfer medium from another source 66 is passed through condenser 58, also for vapor condensing purposes, and is returned to another suitable reservoir 68.

Those oxidation reactor overhead vapors which are not condensed in condensers 56 and 58 are introduced into heat exchanger 30 via conduit 28. The non-condensed vapor stream in conduit 28 has a water-to-solvent weight ratio of about 0.4–0.7.

About 6 to about 8 weight percent of the vaporized reaction medium, supplied by conduit 20 is condensed in heat exchanger 30, and is thereafter discharged therefrom via conduit 78. This condensate contains about 30 to about 60 weight percent water and has a water-to-solvent weight ratio of about 0.4–0.7. The condensed process stream, conveyed by conduit 78, is the aqueous aliphatic acid liquid stream mentioned above. Conduit 78, in turn, conveys this process stream to the above-mentioned pipe-lines 32 and 36, which direct the flow of the aqueous aliphatic acid liquid stream upstream of reactor 14, and/or to storage of processing facility 34, if desired.

Cooling water from a suitable source 80 is passed through heat exchanger 30 for purposes of condensing process vapors contained therein, and is then returned to a suitable cooling tower or reservoir 82. Those process vapors which are not condensed in heat exchanger 30 are conveyed therefrom via conduit 84 int gas cooler 86. Cooling water from another source 88 is passed through gas cooler 86 for gas-cooling purposes, and is thereafter conveyed to reservoir 90.

The 141° C. vapor being introduced into heat exchanger 30 via conduit 28 is reduced in temperature by heat exchanger 30 to about 79° C. (about 174° F.) and is thereafter further cooled by gas cooler 86 to about 44° C. (about 110° F.). This 44° C. vapor is then conveyed substantially at that temperature via a conduit 92 to a suitable storage or processing facility 94.

Facility 92 preferably includes a vented scrubber (not shown) which recovers residual, unreacted p-xylene. The air feed rate from source 16 to reactor 14 is preferably adjusted so that the vent-gas oxygen concentration at the scrubber vent is in the range of about 1 to about 3 volume percent oxygen on a volatile-free basis.

Vapor being introduced into each of condensers 56 and 58, and heat exchanger 30, is substantially at the vapor pressure within reactor 14. Heat exchanger 30 reduces that vapor pressure by about 10 to about 15 percent.

Another advantage of the present invention is that the indirect recycle stream and the trim stream can each be controlled, independent of the other, to maintain water concentration of the reaction medium in reactor 14. However, because the indirect recycle and the water trim streams are both relatively rich in water, the trim-stream rate through conduit 70 is necessarily related to the indirect recycle rate through conduit 36 to achieve a desired rate of water return to reactor 14 via conduits 26 and 36. That is, in operation, the rate or indirect recycle through conduit 36 and the rate of withdrawal through conduit 70 are independently controllably maintained by respective automatic flow-control valves 54 and 74, and the rate of indirect recycle returned to reactor 14 via conduit 36 modulated via automatic flow-control value, to achieve a desired water concentration in reactor 14.

To facilitate water concentration modulation within reactor 14 it has been found advantageous to monitor an indirect-to-direct water ratio defined as the weight of water in conduit 36 to the weight of water in pipelines 24 and 26 taken collectively. This ratio, which in effect is the ratio of water indirectly recycled to reactor 14 to the weight of water directly refluxed into reactor 14, is preferably maintained in a range of about 0.01 to about 0.15, more preferably in a range of about 0.02 to about 0.06. Most preferably, this ratio is maintained at a value of about 0.04.

What has been illustrated and described herein is a method for continuously producing an aromatic carboxylic acid product. While the method of the present invention has been illustrated and described with reference to a preferred embodiment, the present invention is not limited thereto. On the contrary, alternatives, changes or modifications may become apparent to those skilled in the art upon reading the foregoing description. Accordingly, such alternatives, changes and modifications are to be considered as forming a part of the invention insofar as they fall within the spirit and scope of the appended claims.

I claim:

1. In a method for the continuous production of an aromatic carboxylic acid product in a pressurized oxidation reactor by liquid-phase, exothermic oxidation of an aromatic alkyl feed with an oxygen-containing gas, in the presence of an oxidation catalyst and in an aqueous monocarboxylic $C_2$ to $C_6$ aliphatic acid solvent medium, wherein the heat generated during the course of the oxidation is removed from the reactor by vaporization of a portion of the reaction medium and water, wherein the resulting vapors are condensed in part in a reflux loop externally of the oxidation reactor to produce a condensate and a gaseous phase, and wherein at least a portion of the condensate is returned to the oxidation reactor, the improvement comprising a method for controlling within desired limits the concentration of water in the oxidation reactor, which comprises:

partitioning the vapors into a parallel condensate having a relatively lesser water-to-solvent weight ratio and a vapor phase having a relatively greater water-to-solvent weight ratio;

returning the partial condensate directly to the oxidation reactor as a direct reflux stream;

withdrawing the vapor phase from the reflux loop as a vapor stream;

subjecting the withdrawn vapor stream to heat exchange while decreasing the vapor stream pressure to less than the oxidation reactor pressure to thereby produce an aqueous aliphatic acid stream having a water-to-solvent weight ratio greater than that of the direct reflux stream; and combining a predetermined portion of the aqueous aliphatic acid stream with the aromatic alkyl feed upstream of the oxidation reactor as an indirect recycle stream, the predetermined portion being sufficient to thereby control the concentration of water in the oxidation reactor within the aforesaid desired limits therefor.

2. The improvement in accordance with claim 1 wherein water recycled to the oxidation reactor by the indirect recycle stream and by the direct reflux stream is in a weight ratio of about 0.01 to about 0.15.

3. The improvement in accordance with claim 1 wherein water recycled to the oxidation reactor by the indirect recycle stream and by the direct reflux stream is in a weight ratio of about 0.02 to about 0.06.

4. The improvement in accordance with claim 1 wherein water recycled to the oxidation reactor by the indirect recycle stream and by the direct reflux stream is in a weight ratio of about 0.04.

* * * * *

UNITED STATES PATENT OFFICE
CERTIFICATE OF CORRECTION

Patent No. 4,792,621                    Dated   December 20, 1988

Inventor(s)   Kenneth J. Abrams

It is certified that error appears in the above-identified patent and that said Letters Patent is hereby corrected as shown below:

| Col. | Line | |
|---|---|---|
| 1 | 58 | "greater that" should read --greater than-- |
| 3 | 33 | "pipelines 44" should read --pipelines 24-- |
| 4 | 1 | "trieethybenzenes" should read --triemthylbenzenes-- |
| 4 | 53 | "life" should read --life.-- |
| 5 | 27 | "ad" should read --and-- |
| 5 | 64 | "add" should read --and-- |
| 6 | 24 | "int" should read --into-- |
| 7 | 1 | "refuxed" should read --refluxed-- |
| 8 | 1 | "parallel" should read --partial-- |

Signed and Sealed this

First Day of August, 1989

*Attest:*

DONALD J. QUIGG

*Attesting Officer*      *Commissioner of Patents and Trademarks*